United States Patent [19]
Kato

[11] Patent Number: 5,844,122
[45] Date of Patent: Dec. 1, 1998

[54] SENSOR WITH OUTPUT CORRECTING FUNCTION

[75] Inventor: Nobuhide Kato, Ama-gun, Japan

[73] Assignee: NGK Insulators, Ltd., Nagoya, Japan

[21] Appl. No.: 961,196

[22] Filed: Oct. 30, 1997

Related U.S. Application Data

[63] Continuation of Ser. No. 667,863, Jun. 20, 1996, abandoned.

[30] Foreign Application Priority Data

Jun. 26, 1995 [JP] Japan .................................. 7-159684

[51] Int. Cl.[6] .................................................. G01N 27/12
[52] U.S. Cl. .............................. 73/1.06; 73/31.05; 338/34
[58] Field of Search ............................ 73/1 B, 1 G, 4 R, 73/31.06, 23.21, 31.05; 338/195, 308, 307, 309, 34–35, 325

[56] References Cited

U.S. PATENT DOCUMENTS

| | | | |
|---|---|---|---|
| 4,708,012 | 11/1987 | Folk et al. | 73/1 B X |
| 4,766,655 | 8/1988 | Hickox | 73/708 X |
| 4,777,826 | 10/1988 | Rud, Jr. et al. | 73/708 |
| 4,893,508 | 1/1990 | Friedman | 73/335.02 |
| 5,178,016 | 1/1993 | Dauenhauer et al. | 73/727 |
| 5,302,935 | 4/1994 | Chatterjee | 338/34 |
| 5,507,171 | 4/1996 | Mattes et al. | 73/1 B |
| 5,508,491 | 4/1996 | Sherman | 73/204.15 X |
| 5,522,266 | 6/1996 | Nicholson et al. | 73/754 X |
| 5,600,296 | 2/1997 | Kuzuoka et al. | 338/34 X |

FOREIGN PATENT DOCUMENTS

| | | |
|---|---|---|
| 0 309 664 A2 | 5/1989 | European Pat. Off. . |
| 0 461 102 A2 | 12/1991 | European Pat. Off. . |
| 40 41 621 A1 | 7/1992 | Germany . |
| 42 19 551 A1 | 12/1992 | Germany . |
| 4-279831 A | 10/1992 | Japan . |
| 2 285 138 | 6/1995 | United Kingdom . |

OTHER PUBLICATIONS

Patent Abstracts of Japan, vol. 012, No. 029 (P–660), 28 Jan. 1988 & JP–A–62 182647 (Honda Motor Co Ltd), 11 Aug. 1987, abstract.
Patent Abstracts of Japan, vol 018, No. 250 (P–1736), 12 May 1994 & JP–A–06 034471 (Fujikura Ltd), 8 Feb. 1994, abstract.
Patent Abstracts of Japan, vol. 95, No. 7, 31 Aug. 1995 & JP–A–07 111206 (Nippondenso Co Ltd), 25 Apr. 1995, abstract.
Patent Abstracts of Japan, vol. 010, No. 341 (P–517), 18 Nov. 1986 & JP–A–61 144525 (Omron Tateisi Electronics Co), 2 Jul. 1986, abstract.

*Primary Examiner*—Michael Brock
*Attorney, Agent, or Firm*—Kubovcik & Kubovcik

[57] ABSTRACT

A sensor has a voltage output circuit and a potentiometric resistor for dividing the voltage of the voltage output circuit. The resistance of the potentiometric resistor is regulated by trimming in order to regulate the output voltage of the sensor. A sensor has a voltage output circuit and a serial resistor connected in series with the voltage output circuit. The total resistance of the voltage output circuit and the serial resistor is regulated by trimming so as to have a certain relation with the output voltage of the voltage output circuit. The resistance of the potentiometric resistor or the serial resistor may be 100 times or more as much as the resistance of the voltage output circuit. The voltage output circuit may comprise a resistor having a positive resistance temperature coefficient, a semiconductor whose resistance changes in accordance with a gas concentration, or a piezoelectric element for converting a stress into a piezoelectric signal. According to the sensor, the unevenness of the output voltage can be reduced.

5 Claims, 4 Drawing Sheets

SENSOR WITH OUTPUT CORRECTING FUNCTION

This application is a continuation of application Ser. No. 08/667,863, filed Jun. 20, 1996, now abandoned.

BACKGROUND OF THE INVENTION (i) Field of the Invention

The present invention relates to a sensor for outputting voltages, and more particularly, it relates to a sensor by which uneven outputs of voltages can be corrected. The sensor of the present invention can be used to measure a temperature, a gas flow rate, a gas concentration or the like, or to detect a strain, particles or the like.

(ii) Description of the Related Art

Heretofore, various sensors for outputting voltages are known. For instance, in a gas sensor in which a metal oxide semiconductor is used, a current is applied to the metal oxide semiconductor whose resistance value changes in accordance with the concentration of a gas to output a voltage generated in the metal oxide semiconductor, whereby the gas concentration is measured. In a temperature sensor in which a resistor such as platinum having a positive resistance temperature coefficient is used, a current is applied to the resistor, and a voltage generated in the resistor is output, whereby the temperature is measured. In a sensor in which a piezoelectric element is used, the piezoelectric element converts a mechanical stress into a piezoelectric signal, and then outputs its voltage.

When any of these sensors is used, the sensor is connected to another electronic device, a central processing unit or the like, and the electronic device, the central processing unit or the like usually converts a voltage signal. For instance, a resistance value R of a resistor having a positive resistance temperature coefficient (which is synonymous with a voltage value, when measurement is made by applying a constant current) is represented by $R=R_o(1+\alpha t-\beta t^2)$ wherein t is a temperature and $R_o$ is a resistance value at 0° C. In this connection, $R_o$ is not limited to the resistance value at 0° C., and a known resistance at a specific temperature can also be used. Therefore, as a premise of measuring the temperature or the like by the electronic device, the central processing unit or the like, it is required that the resistance value at a certain temperature of the resistor in the specific sensor connected to the electronic device or the like is input to the electronic device or the like. Furthermore, when the sensors are attached to automobiles on such a mass production line as in an assembly plant of the automobiles, the resistance value of the resistor in each sensor is required to be promptly input to the electronic device or the like. For example, it is impractical that the resistance value of the resistor is input to the computer of each automobile by way of a keyboard.

However, in the process of manufacturing the sensors, the output voltages of the resistor, the semiconductor, the piezoelectric element or the like inevitably scatter to some extent. For example, if the resistor, the semiconductor, the piezoelectric element or the like is in the state of a layer, the resistor can often be formed by printing its pattern on the surface of a ceramic green sheet, and then baking the green sheet having the resistor pattern. The resistance value of the thus formed resistor, semiconductor, piezoelectric element or the like typically has a deviation of ±10%.

Japanese Patent Application Laid-open No. 279831/1992 has described a technique of trimming a platinum resistor by means of laser irradiation in order to minimize the unevenness of the resistor. However, when the resistor is trimmed by the laser irradiation, the temperature of the resistor rises. Since the resistor has a large resistance temperature coefficient, it is difficult to heighten the precision of the resistance value of the resistor, so that the resistance values of sensors largely scatter sometimes.

SUMMARY OF THE INVENTION

An object of the first aspect of the present invention is to provide a sensor which can decrease the unevenness of the resistance values of the whole sensor. An object of the second aspect of the present invention is to provide a sensor by which the resistance value of a resistor can be precisely and promptly input to another electronic device, a central processing unit or the like.

The first aspect of the present invention is directed to a sensor having a voltage output circuit and a potentiometric resistor for dividing the voltage of the voltage output circuit, the resistance of the potentiometric resistor being regulated by trimming in order to regulate the output voltage of the sensor.

In the present invention, the resistance of the potentiometric resistor is preferably 100 times or more, more preferably 1000 times or more as much as the resistance of the voltage output circuit.

It is preferred that the voltage output circuit comprises a resistor having a positive resistance temperature coefficient, current leads for applying a current to the resistor and voltage leads for detecting the voltage of the resistor, and the resistance of the potentiometric resistor is regulated by trimming so that an output voltage at a time when a predetermined current is allowed to flow through the resistor may be a predetermined value.

Furthermore, it is preferred that the voltage output circuit comprises a semiconductor whose resistance changes in accordance with a gas concentration and voltage leads for detecting the voltage of the semiconductor, and the resistance of the potentiometric resistor is regulated by trimming so that an output voltage at a time when the semiconductor is exposed to a predetermined gas concentration may be a predetermined value.

In addition, it is preferred that the voltage output circuit comprises a piezoelectric element for converting a stress into a piezoelectric signal and voltage leads for detecting the piezoelectric signal of the piezoelectric element, and the resistance of the potentiometric resistor is regulated by trimming so that an output voltage at a time when the piezoelectric element is subjected to a predetermined stress may be a predetermined value.

According to the second aspect of the present invention, there is provided a sensor which comprises a voltage output circuit and a serial resistor connected in series with the voltage output circuit, the total resistance of the voltage output circuit and the serial resistor being regulated by trimming so as to have a certain relation with the output voltage of the voltage output circuit.

In the present invention, the output voltage of the voltage output circuit is preferably proportional to the total resistance of the voltage output circuit and the serial resistor.

The resistance of the serial resistor is preferably 100 times or more as much as that of the voltage output circuit.

Moreover, the voltage output circuit preferably comprises a resistor having a positive resistance temperature coefficient, voltage leads for applying a current to the resistor and voltage leads for detecting the voltage of the resistor. The resistance of the serial resistor may be regulated by trimming so that the total resistance of the resistor, the serial resistor and the voltage leads may be proportional to the resistance of the resistor.

The voltage output circuit preferably has a semiconductor whose resistance changes in accordance with a gas concentration.

The voltage output circuit preferably has a piezoelectric element for converting a stress into a piezoelectric signal.

In the present invention, at least a part of the surface of a ceramic substrate is preferably covered with the potentiometric resistor or the serial resistor. Furthermore, it is preferred that the resistor is located at an end of the ceramic substrate, and the potentiometric resistor or the serial resistor is located at the other end of the ceramic substrate.

Additionally, in the present invention, the potentiometric resistor or the serial resistor is preferably covered with glass. The resistance of the potentiometric resistor or the serial resistor is preferably 100 times or more, more preferably 1000 times or more as much as that of the resistor.

DETAILED DESCRIPTION OF THE PREFERRED EMBODIMENTS

According to the first aspect of the invention, the potentiometric resistor may be connected in parallel with the resistor. The output voltage of the sensor at a time when a predetermined current is applied to the current leads is regulated to a predetermined value by the laser trimming of the potentiometric resistor. Thus, since the unevenness of the output voltage of the sensor is slight, the output voltages of the sensor can collectively be input in the electronic device, the central processing unit or the like, if these output voltages are specific values. Alternatively, the electronic device, the central processing unit of the like may be regulated so that the output voltages of the sensor may correspond to specific values.

The potentiometric resistor has a resistance temperature coefficient smaller than the resistor, and therefore when the potentiometric resistor is subjected to laser irradiation, the error of resistance values of the potentiometric resistor caused by heat generated in the potentiometric resistor is smaller as compared with the case of trimming of the resistor by the laser.

According to the second aspect of the present invention, the resistance of the serial resistor may be regulated by trimming so that the total resistance of the resistor, the serial resistor and the voltage leads may have a certain relation with the resistance of the resistor. For example, when the resistance of the resistor is 10 ohms, the resistance of the serial resistor is regulated so that the total resistance may be 10 kilo-ohms which is 1000 times as much as 10 ohms. Then, the electronic device, the central processing unit or the like can detect the total resistance of the sensor and can calculate the resistance of the resistor on the basis of the above-mentioned certain relation. For example, if it is detected that the total resistance of the resistor elements is 10 kilo-ohms, the resistance of the resistor is 10 ohms by calculation.

This certain relation is preferably that the total resistance of the resistor, the serial resistor and the voltage leads is proportional to the resistance of the resistor.

The potentiometric resistor may be connected in parallel to the resistor, for example, by way of voltage leads. Unlike the resistor, the potentiometric resistor preferably has a small resistance temperature coefficient. Similarly, the serial resistor preferably has a small resistance temperature coefficient unlike the resistor.

As the potentiometric resistor or the serial resistor, there can be used, for example, a ceramic substrate on which a metal or a metal oxide is printed, a glass in which the particles of a metal or a metal oxide are dispersed, or a thin film or a fine wire comprising a metal or a metal oxide.

The potentiometric resistor or the serial resistor preferably covers at least a part of the surface of the substrate. According to such a constitution, the potentiometric resistor can be trimmed by laser or the like to regulate the output voltage from the resistor at the time of the application of a current. For example, in the case of a temperature sensitive resistor, the resistance value of the potentiometric resistor can be regulated to obtain the constant output voltage by trimming the potentiometric resistor by laser, while a counter electromotive force generated at the application of a predetermined current to the resistor at a predetermined temperature (e.g., 25° C.) is detected as the output voltage. Thus, the output voltage of the sensor at the predetermined temperature can be substantially uniformized to a certain level.

In addition, since the potentiometric resistor or the serial resistor can be arranged at a position which does not come in contact with an atmosphere where the temperature is measured, the potentiometric resistor scarcely deteriorates, so that the resistance value of the potentiometric resistor scarcely changes with time.

The resistance value of the potentiometric resistor or the serial resistor is preferably 100 times or more, more preferably 1000 times or more as much as that of the resistor in order to heighten the precision of the sensor. Furthermore, the potentiometric resistor or the serial resistor is preferably located at a position separated to some extent from the resistor in order to protect the potentiometric resistor or the serial resistor from the heat transmitted from the environment for the temperature measurement or the resistor. For example, it is preferred that the resistor may be located at one end of the ceramic substrate, and the potentiometric resistor or the serial resistor may be located at the other end of the ceramic substrate.

Moreover, the potentiometric resistor or the serial resistor is preferably covered with glass in order to improve its durability. According to such a constitution, even when a high temperature is measured by the sensor, the glass cover layer of the potentiometric resistor or the serial resistor can sufficiently keep the durability, because the potentiometric resistor or the serial resistor can be located at a position where it is scarcely affected by the high temperature.

The covering the potentiometric resistor or the serial resistor with the glass can be accomplished by forming a slurry of a glass powder such as lead borosilicate glass, allowing this slurry to adhere to the surface of the potentiometric resistor or the serial resistor by immersion, blade coating or spray coating, drying the slurry on this surface, and then baking it.

Next, description will be made mainly about an embodiment in which the resistor having a positive resistance temperature coefficient is used.

The entire substrate is preferably made of a ceramic material. However, it is sufficient for the present invention that the temperature sensitive portion where the resistor is buried is made of the ceramic material. Preferably, the ceramic material for use in the ceramic substrate is electrically more insulating, as compared with the resistance value of the resistor. Additionally, the ceramic material preferably has a low thermal conductivity in order to improve the precision of the sensor. Examples of the usable material for the ceramic substrate include alumina, steatite and mullite. The whole ceramic substrate is preferably made of one kind of material, but the material of a portion of the ceramic substrate may be different from that of the other portion thereof. The ceramic substrate is preferably so dense that gas molecules cannot pass therethrough.

The shape of the ceramic substrate or the temperature sensitive portion is not always plate-like but rod-like or pipe-like. The shape of the ceramic substrate is preferably such that the potentiometric resistor is not affected by the temperature which is measured by the resistor, i.e., such that the thermal conductivity of the ceramic substrate is minimized.

The resistor contains a metal having a positive resistance temperature coefficient. Examples of the usable metal include platinum, rhodium, nickel and tungsten, and above all, platinum is particularly preferable. The resistor may be made of this metal or a thermite of an alloy containing the metal and a ceramic material. Needless to say, the resistor may be made of a simple substance of this metal or an alloy containing the metal. This sensor measures the temperature by utilizing the property of the resistor that its electric resistance varies in accordance with a temperature change.

In the sensor of the present invention, a current may be applied to the resistor to detect a voltage. In this case, even if leads, terminal pads and the like have fairly high resistance values, the precision of the temperature measurement can be maintained. In this case, the sensor preferably has voltage detection leads for detecting the voltage generated when the electric current is applied to the resistor. The voltage detection leads are electrically connected to the resistor. Alternatively, a voltage may be applied to the resistor to detect a current.

The resistor, the leads and the terminal pads of the sensor are preferably formed on the ceramic substrate by printing. Alternatively, blade coating, spray coating or the like may be utilized.

Now, the present invention will be described with reference to embodiments. However, the scope of the present invention should not be limited to these embodiments. In the first place, a sensor of regarding the first aspect of the present invention will be described referring to drawings.

Embodiment 1

Figure 1:
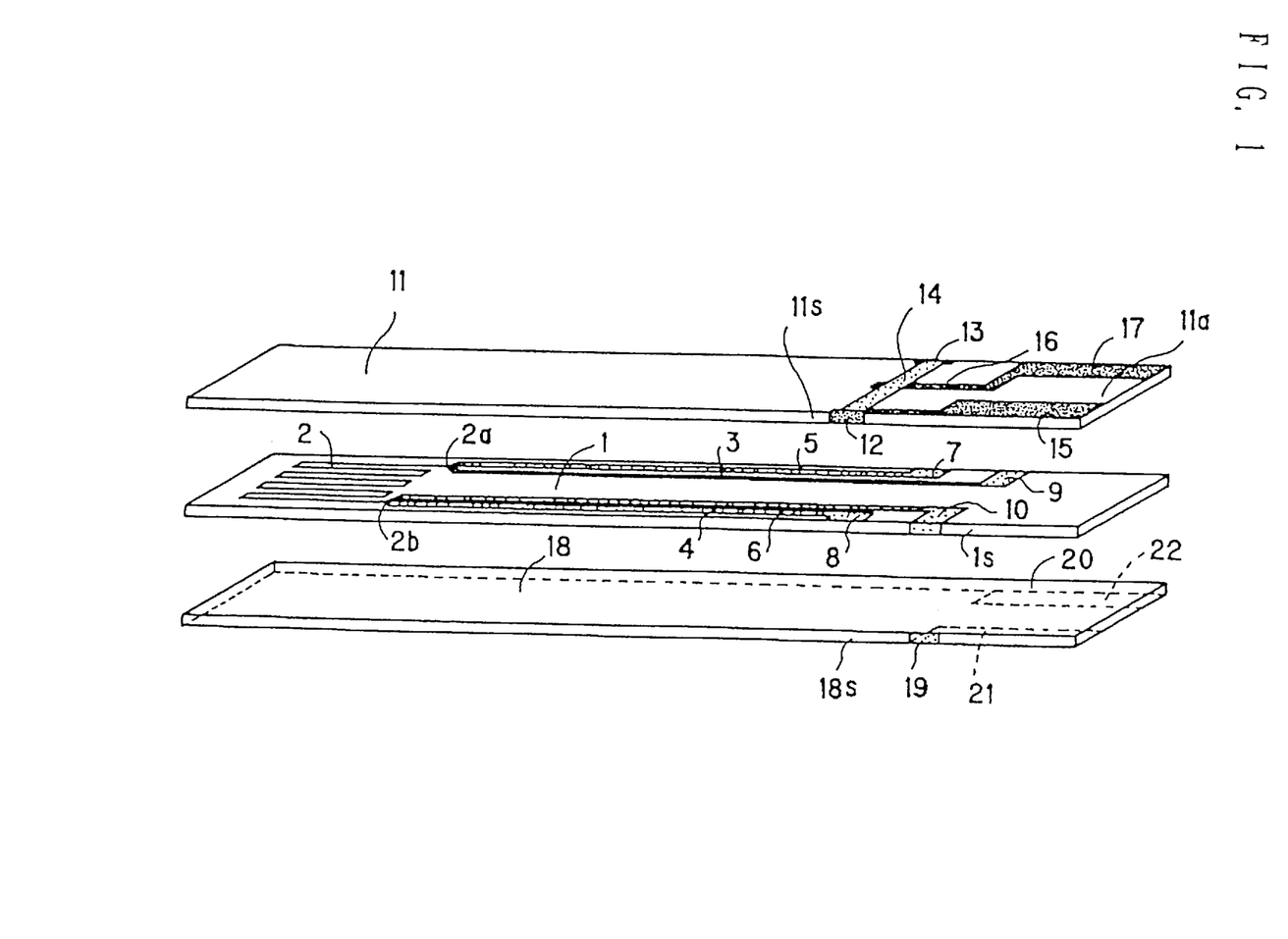
FIG. 1 is an exploded schematic perspective view of one embodiment of a sensor according to the first aspect of the present invention.

FIG. 1 is an exploded perspective view of the first embodiment of the present invention. Furthermore, FIG. 1 can be understood to be a perspective view of a process for manufacturing one embodiment of the present invention.

A resistor 2 made of a mixed paste of platinum and alumina is printed on the surface of a ceramic substrate 1. In FIG. 1, the ceramic substrate 1 is made of raw alumina and not baked.

On the surface of the ceramic substrate 1, a pair of current leads 3, 4 connected to both the ends of the resistor 2 are printed. The current leads 3, 4 are provided at the other ends thereof with connection pads 9, 10 for securing conduction on sides 1s of the ceramic substrate 1.

On the surface of the ceramic substrate 1, a pair of voltage detection leads 5, 6 connected to both the ends of the resistor 2 are printed. The voltage detection leads 5, 6 are provided at the other ends thereof with connection pads 7, 8 for securing conduction on the sides 1s of the ceramic substrate 1. Furthermore, an end 2a of the resistor 2 is branched to the current lead 3 and the voltage detection lead 5, and another end 2b of the resistor 2 is branched to the current lead 4 and the voltage detection lead 6.

The current leads 3, 4, the voltage detection leads 5, 6 and the connection pads 7, 8, 9, 10 are made of, for example, a mixed paste of platinum and alumina. It is preferred that they are simultaneously printed in a step where the resistor is printed. However, the material of the current leads 3, 4, the voltage detection leads 5, 6 and the connection pads 7, 8, 9, 10 need not always be the same as that of the resistor 2, so long as they can be electrically connected to the resistor 2.

Another ceramic substrate 11 is preferably made of the same material as the ceramic substrate 1. In FIG. 1, the ceramic substrate 11 is, for example, raw alumina. On the sides 11s of the ceramic substrate 11, there are printed side conductors 12, 13 for electrically connecting them to the connection pads 7, 8.

A terminal pad 15 is electrically connected to the side conductor 12. Between the side conductors 12, 13, a potentiometric pad 16 is printed. This potentiometric pad 16 may be arranged substantially at the middle of the side conductors 12, 13. The potentiometric pad 16 is connected to a terminal pad 17. The terminal pad 15 does not intersect with the terminal pad 17.

The terminal pads 15, 17 and the potentiometric pad 16 are printed on the surface of an end portion 11a of the ceramic substrate 11. The terminal pads 15, 17 and the potentiometric pad 16 are made of a mixed paste of platinum and alumina. The material of the terminal pads 15, 17 and the potentiometric pad 16 need not always be the same as that of the resistor 2.

Another ceramic substrate 18 is preferably made of a material the same as that of the ceramic substrate 1. In FIG. 1, the ceramic substrate 18 is, for example, raw alumina. On sides 18s of the ceramic substrate 18, side conductors 19, 20 for electrically connecting to the connection pads 9, 10 are printed so as to extend to the back surface of the ceramic substrate 18. The respective side conductors 19, 20 are connected to terminal pads 21, 22 printed on the back surface of the alumina substrate 18. The side conductors 19, 20 and the terminal pads 21, 22 are made of, for example, a mixed paste of platinum and alumina. However, the material of the side conductors 19, 20 and the terminal pads 21, 22 is not always the same as that of the resistor 2.

These three ceramic substrates 1, 11, 18 are laminated on one another, pressed, and then baked at 1600° C. into a body. The baking operation is preferably conducted in a reducing atmosphere when the resistor 2 is made of tungsten or nickel, or it may be conducted either in the reducing atmosphere or in an oxidizing atmosphere when the resistor 2 is made of platinum or rhodium.

In order to connect the side conductors 12, 13 to each other, a potentiometric resistor 14 comprising a mixture of ruthenium oxide and glass is printed, and then baked. This potentiometric resistor 14 covers at least a part of the potentiometric pad 16 to electrically connect to the potentiometric pad.

Next, a predetermined current is applied to the resistor by way of the terminal pads 21, 22, and the resistance of the potentiometric resistor is regulated by trimming so that a detected voltage may be a predetermined value, while the voltage is detected by the terminal pad 15, 17. At this time, the current to be applied may be either a direct current or an alternating current.

Figure 2:
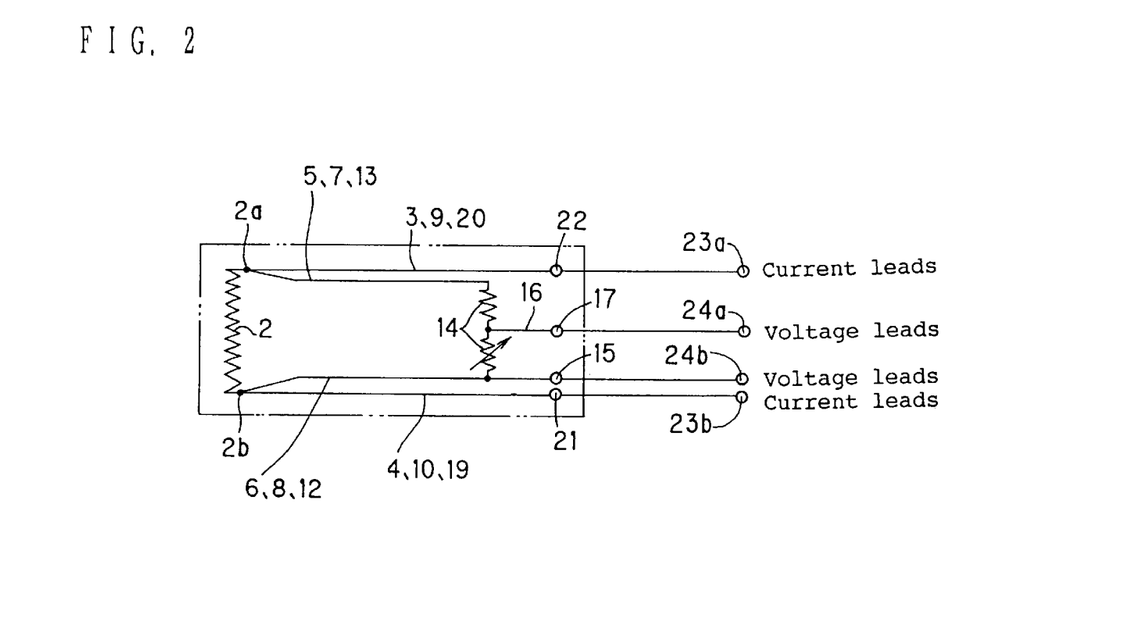
FIG. 2 is an electric circuit diagram of the sensor according to the first aspect of the present invention.

In FIG. 2, the potentiometric resistor 14 is connected in parallel with the resistor 2. Thus, a part of the voltage of the potentiometric resistor 14 is output from the terminal pads 15, 17.

Figure 3:
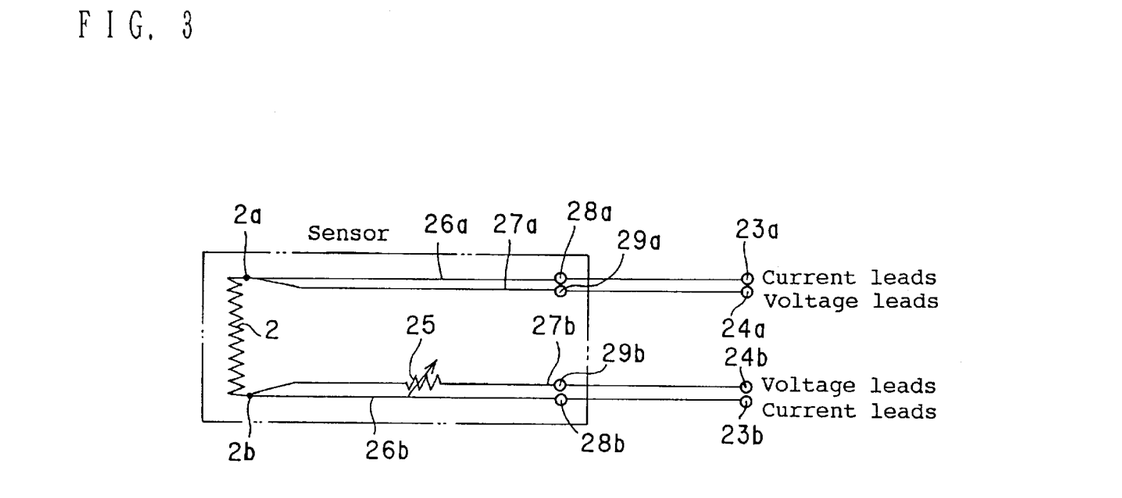
FIG. 3 is an electric circuit diagram of a sensor according to the second aspect of the present invention.

In one embodiment of a sensor regarding the second aspect of the present invention, the potentiometric resistor 14 in the embodiment of FIG. 1 is replaced with a serial resistor 25. Furthermore, the leads and the side conductors are formed so that the resistor 2 and the serial resistor 25 are connected in series with each other by way of a voltage lead 27b. For example, the voltage lead 27b which is one of a pair of voltage leads is connected to a voltage terminal 29b which is one of a pair of voltage terminals by way of the serial resistor 25, and the other voltage lead 27a is connected to the other voltage terminal 29a without connecting to the serial resistor 25.

In FIG. 3, the resistor 2 is connected in series with the serial resistor 25 by way of the voltage lead 27b. In the second aspect of the present invention, the resistance of this serial resistor 25 is regulated by trimming in accordance with the resistance value of the resistor 2. For example, if the resistance value of the resistor 2 is 10Ω, that of the serial resistor 25 is regulated to 10 kΩ, and if the resistance of the resistor 2 is 20 kΩ, that of the serial resistor 25 is regulated to 20 α.

As a technique of this regulation, in the first place, a predetermined current is allowed to flow through the resistor 2 by way of a pair of current leads 26a, 26b to detect a voltage by way of the voltage leads 27a, 27b, whereby the resistance of the resistor 2 can be measured. For example, $R_o$ of the resistor 2 can be measured. Here, the current does not substantially flow through the voltage leads, and therefore the voltage which is applied to the serial resistor 25 is negligible.

Next, the resistance of the serial resistor 25 is regulated by trimming. An ohmmeter is connected to a pair of voltage terminals 29a, 29b to detect the total resistance of the resistor 2, the serial resistor 25 and the voltage leads 27a, 27b. Then, the resistance value of the serial resistor 25 is regulated by trimming so that this total resistance may have a certain relation with the resistance of the resistor 2. Typically, this total resistance is regulated so as to be proportional to the resistance of the resistor 2.

When the information of the sensor is fed to another electric circuit, a central processing unit, an interface or the like, voltage terminals 29a, 29b are connected to the electric circuit or the like to detect the total resistance of the resistor 2, the serial resistor 25 and the voltage leads 27a, 27b. Then, the resistance of the resistor can be calculated backward on the basis of the total resistance in accordance with the above-mentioned certain relation.

When the sensor is used to measure the temperature, a current is applied to it by way of the current terminals 28a, 28b to detect the resistance of the resistor 2 by way of the voltage terminals 29a, 29b.

The resistance value of the serial resistor is preferably set to a sufficiently large value with respect to the resistance of the resistor, and so the resistance of the serial resistor is preferably 100 times or more, more preferably 500 times or more, most preferably 1000 times or more as much as that of the resistor. According to this constitution, a read-out resistance (a combined resistance) is not affected by a resistance change due to the temperature change of the resistor 2.

Figure 4:
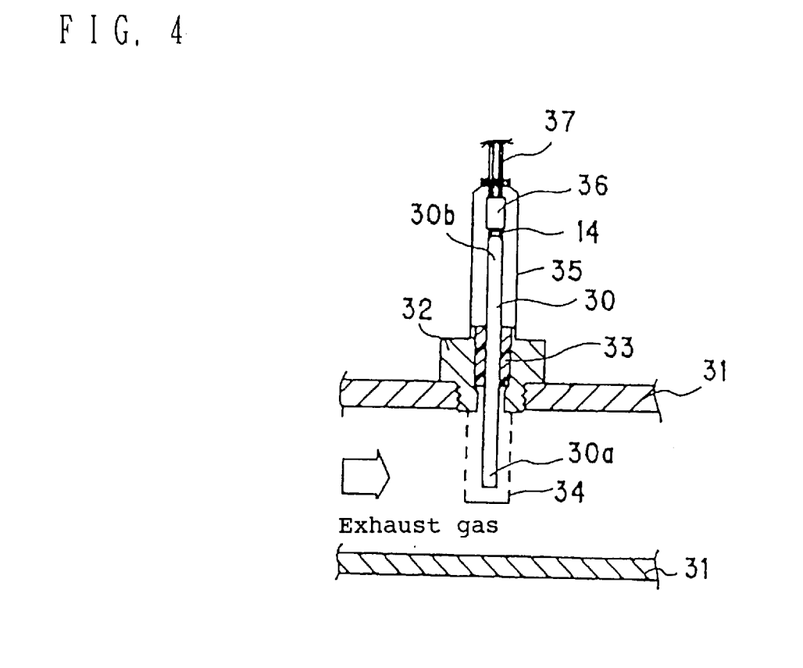
FIG. 4 is a sectional view showing a use state of a sensor according to the present invention.

An embodiment in which the sensor 30 of the present invention is used in an exhaust pipe 31 of an automobile is shown in FIG. 4. The sensor 30 may be the sensor regarding the first aspect of the present invention or the sensor regarding the second aspect of the present invention. The sensor 30 is attached to the exhaust pipe 31 by way of a housing 32. At this time, the end portion 30a where the resistor 2 is buried is projected into the exhaust pipe 31, and another end portion 30b having the potentiometric resistor 14 is arranged outside the exhaust pipe 31. A buffer member 33 for the sensor 30 is disposed in the housing 32.

Since the substrate of the sensor 30 made of the ceramic material is susceptible to impact, the end portion 30a is covered with a protective cover 34. This protective cover 34 is provided with a plurality of through-holes, so that a gas to be measured such as an exhaust gas is allowed to pass through the protective cover 34.

The other end portion 30b of the sensor 30 is connected to a connector 36, through which electrical signals detected at the terminal pads 15, 17, 21, 22 can be transmitted to a line 37. The end portion 30b of the sensor 30 and the connector 36 are inserted through a casing 35.

In the above-mentioned embodiment, the three ceramic substrates are laminated on one another, pressed, and then baked into one body to form the ceramic substrate. However, the three ceramic substrates are not essential. For example, the ceramic substrate 18 may be omitted, and the terminal pads electrically connected to the respective connection pads 9, 10 may be printed on the back surface of the ceramic substrate 1.

Now, a preferable embodiment of the present invention will be described below.

The ceramic substrate is preferably made of an electrically insulating oxide ceramic material such as $Al_2O_3$. The purity of $Al_2O_3$ is preferably 99% or more, more preferably 99.9% or more. Thus, it can be prevented that impurities react with the resistor at a high temperature to change the resistance value of the resistor and the resistance-temperature properties.

In particular, the content of $SiO_2$ should be as low as possible. The sintering properties of the ceramic material can be improved by adding $Y_2O_3$ or $ZrO_2$. $Y_2O_3$ or $ZrO_2$ can safely be used, because neither of them reacts with a noble metal which can be used as the resistor.

A temperature at which a green sheet, the resistor printed thereon, the leads and the like are simultaneously baked is preferably 1500° C. or more. Thus, when the sensor is used at a high temperature, a resistance change caused by the resintering of the metal contained in the resistor can be reduced.

The resistor is preferably made of a thermite comprising the same ceramic material as the ceramic substrate and a noble metal having a positive resistance temperature coefficient such as Pt, Rh or Pd or its alloy. When the same ceramic material as the ceramic substrate is used, the adhesive properties between the resistor and the ceramic substrate can be enhanced.

When the resistor contains Ni or a low-melting noble metal having a positive resistance temperature coefficient such as Au or Ag, the thermite resistor is easily sintered at the time of the baking of the ceramic substrate, and during use at a high temperature, the change in the resistance value decreases preferably.

Reference has just been made above mainly about the sensor having the temperature sensitive resistor. Next, a sensor having a piezoelectric element will be described below. For example, when particles are detected, the particles in a fluid come in contact with a detecting portion or an oscillating portion, and the detecting portion or the oscillating portion oscillates. Then, this oscillating is converted into an electric signal by a piezoelectric film of the detecting portion, and a pair of electrodes which nips the piezoelectric film outputs this electric signal.

Figure 5:
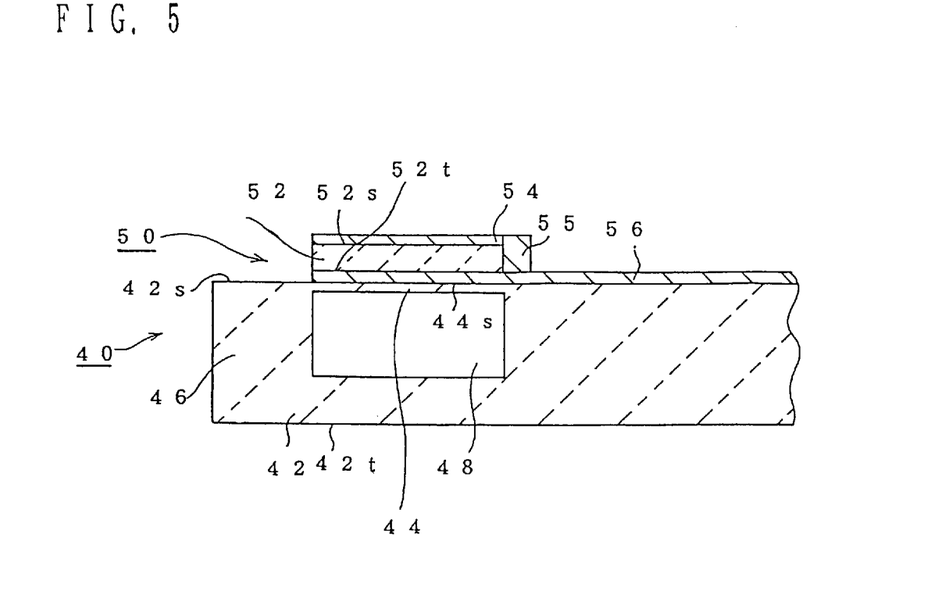
FIG. 5 is a sectional view of a sensor into which the present invention can be applied.
Figure 6:
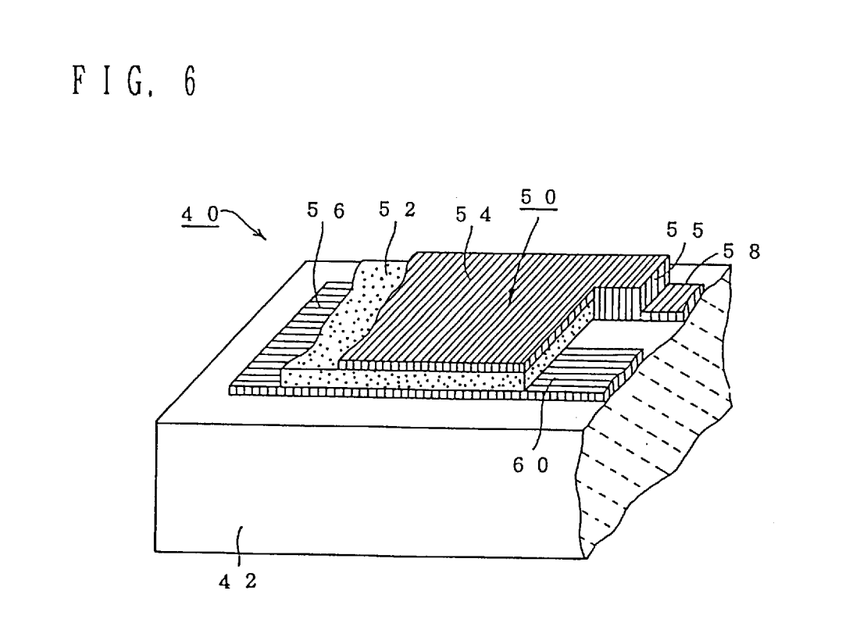
FIG. 6 is an illustrative perspective view of the sensor in FIG. 5.

FIG. 5 is an illustrative sectional view of a sensor 40 having the piezoelectric element. FIG. 6 is a perspective view of the sensor 40 of FIG. 1, but for the convenience of the description, a piezoelectric film 52 and an upper electrode 54 of the sensor 40 are partially cut away. In the sensor 40, the piezoelectric film 52 corresponds to the resistor 2 in FIG. 2 or 3. Furthermore, the current leads 3, 4, 9, 10, 19, 20 and the current terminals 21, 22 are unnecessary. The piezoelectric film 52 is connected in parallel with a potentiometric resistor by way of voltage leads 58 and 60. Alternatively, the piezoelectric film 52 may be connected in series with a serial resistor by way of either of the leads 58, 60. The voltage leads 58, 60 in FIG. 5 correspond to the voltage leads 27a, 27b in FIG. 2 or 3, respectively.

As the potentiometric resistor or the serial resistor, for example, a thin film can be used which is formed by printing and baking a thermite of a metal oxide such as ruthenium oxide and a ceramic material. The potentiometric resistor or the serial resistor is preferably covered with a glass layer.

The sensor 40 comprises a substrate 42 and a detecting portions 50 mounted on an oscillating portion 44 of the substrate 42.

In the substrate 42, the oscillating portion 44 and a stationary portion 46 are integral, and the oscillating portion 44 and the stationary portion 46 constitute parts of the substrate 42. A detecting portion 50 is mounted on the oscillating portion 44, and on the other hand, the stationary portion 46 is arranged under the oscillating portion 44 so as to surround the oscillating portion 44.

However, the oscillating portion and the stationary portion do not have to be the parts of the substrate, and for example, the stationary portion made of a metal may fix another oscillating portion made of a ceramic material. In the case that the stationary portion is made of the metal, the surface of the oscillating portion connected to the stationary portion may be metallized, and the resulting metallized layer may be brazed. Alternatively, the oscillating portion may be fixed by the mere press of the metal. The stationary portion may be made of a metal such as stainless steel or iron.

The substrate 42 is provided with a closed space 48 as a vacancy so that the oscillating portion 44 may be thin. The detecting portion 50 is disposed, confronting the closed space 48. In the present invention, however, the vacancy is not limited to the closed space, and the vacancy may be a recess extending from the surface 42t of the substrate 42 to the oscillating portion 44.

When particles are detected by the sensor 40, the oscillating portion 44 oscillating together with the detecting portion 50 vertically toward the detecting portion 50 and the space 48. For the sake of the suitable oscillating, the oscillating portion 44 is preferably plate-like, and in this case, the thickness of the plate is preferably in the range of 1 to 400 $\mu$m, more preferably 3 to 50 $\mu$m, most preferably 5 to 20 $\mu$m. If the thickness of the oscillating portion 44 is more than 400 $\mu$m, the sensitivity of the oscillating portion 44 is poor, and if it is less than 1 $\mu$m, mechanical strength deteriorates.

The oscillating portion 44 is preferably made of a highly heat-resistant material. Thus, the deterioration of the oscillating portion 44 by heat can be prevented during the formation of the piezoelectric film 52, if the detecting portion 50 is directly mounted on the oscillating portion 44 without using a material having a poor heat resistance therebetween such as an organic adhesive. In addition, when a lubricant such as an oil is used in the sensor, the oscillating portion comes in contact with an organic solvent contained in the lubricant, or the lubricant becomes acidic or basic. Therefore, the oscillating portion is preferably made of a chemically stable material.

In addition, the second electrode covering at least a part of the oscillating portion 44, the leads connected to the first and second electrodes and the lead terminals are electrically conductive, and hence the oscillating portion 44 is preferably made of an electrically insulating material. Therefore, the oscillating portion 44 may be made of a highly heat-resistant metal, and the surface of this metal may be covered with a ceramic material, but the oscillating portion 44 is most preferably made of the ceramic material. Examples of the usable ceramic material for the oscillating portion include stabilized zirconium oxide, aluminum oxide, magnesium oxide, mullite, aluminum nitride, silicon nitride and glass. Above all, stabilized zirconium oxide is preferable, because it can exert a high mechanical strength, even if the oscillating portion is thin, and its chemical reactivity with the piezoelectric film and the electrodes is low.

Stabilized zirconium oxide includes stabilized zirconium oxide and partially stabilized zirconium oxides. Since stabilized zirconium oxide has a crystalline structure such as a cubic system, phase transition does not occur. On the other hand, zirconium oxide gives rise to the phase transition between a monoclinic system and a tetragonal system at about 1000° C., and during this phase transition, cracks take place sometimes. Thus, stabilized zirconium oxide preferably contains 1 to 30 mol % of a stabilizer selected from the group consisting of calcium oxide, magnesium oxide, yttrium oxide, scandium oxide, ytterbium oxide, cerium oxide and oxides of rare earth metals. In order to enhance the mechanical strength of the oscillating portion, yttrium oxide is preferable as the stabilizer. At this time, the amount of yttrium oxide is preferably in the range of 1.5 to 6 mol %, more preferably 2 to 4 mol %. The principal crystal system may be a tetragonal system, a mixed phase of the tetragonal system and a cubic system, a mixed phase of the cubic system and a monoclinic system, a mixed phase of the tetragonal system and the monoclinic system, or a mixed phase of the cubic system, the tetragonal system and the monoclinic system. Above all, the tetragonal system or the mixed phase of the tetragonal system and the cubic system is preferable from the viewpoint of mechanical strength, toughness and durability.

The ceramic material for the oscillating portion 44 preferably contains 0.5 to 5% by weight, more preferably 1 to 3% by weight of silicon oxide. Thus, when the detecting portion 50 is formed by a heat treatment, silicon oxide can suppress an excessive reaction between the oscillating portion 44 and the detecting portion 50 to obtain good piezoelectric characteristics.

When made of the ceramic material, the oscillating portion 44 is constituted of a large number of crystalline particles, but in order to enhance the mechanical strength of the oscillating portion, the average particle size of the crystalline particles is preferably in the range of 0.05 to 2 μm, more preferably 0.1 to 1 μm.

The stationary portion 46 fixes at least a part of the oscillating portion 44 or at least a part of the periphery of the oscillating portion 44 so that the oscillating portion 44 can oscillate. In the embodiment of FIG. 1, the stationary portion 46 is preferably made of the ceramic material, which may be the same ceramic material as the material of the oscillating portion 44 or may be different therefrom. Examples of the ceramic material for the stationary portion 46, which is the same as the material for the oscillating portion 44, include stabilized zirconium oxide, mullite, aluminum oxide, magnesium oxide, aluminum nitride, silicon nitride and glass.

No particular restriction is put on the profile of the closed space 48 which is the vacancy. The horizontal or vertical cross section of the vacancy may be a circular form, an elliptic form, a polygonal form such as a square form or a rectangular form, or a composite form obtained by combining any of these forms. If the cross section is the polygonal form, beveling is preferably given so that the corners may be rounded.

The detecting portion 50 comprises a piezoelectric film 52, a first electrode 54 covering at least a part of the outer surface 52s of the piezoelectric film 52, and a second electrode 56 covering at least a part of the inner surface 52t of the piezoelectric film 52. The second electrode 56 covers at least a part of the surface 44s of the oscillating portion 44.

The piezoelectric film 52 microscopically gives rise to dielectric polarization in accordance with a stress, and macroscopically outputs an electric signal, for example, an electric charge or a voltage. At this time, on the piezoelectric film, a bending displacement preferably appears in its thickness direction. When the particles come in contact with the first electrode and/or the oscillating portion, the piezoelectric film 52 oscillating together with the oscillating portion 44 in the thickness direction of the piezoelectric film 52, and the stress is added to the piezoelectric film 52 by this oscillation.

The thickness of the piezoelectric film is preferably in the range of 1 to 100 μm, more preferably 5 to 50 μm, most preferably 5 to 30 μm. If the film thickness is more than 100 μm, the sensitivity of the piezoelectric film deteriorates, and if it is less than 1 μm, reliability can scarcely be secured.

The piezoelectric film can suitably be made of a piezoelectric ceramic material, but it may be made of an electrostrictive ceramic material or a ferroelectric ceramic material. In addition, it may be made of a material which requires or does not require a polarization process.

Examples of the ceramic material for the piezoelectric film include lead zirconate, lead magnesium-niobate, lead nickel-niobate, lead zinc-niobate, lead manganese-niobate, lead antimony-stannate, lead titanate, lead manganese-tungstate, lead cobalt-niobate, barium titanate and mixtures thereof. Needless to say, a ceramic material containing, as a main component, 50% by weight or more of any of these compounds is also usable. The ceramic material containing lead zirconate is preferably used. To any of the above-mentioned ceramic materials, there can be further suitably added lanthanum, calcium, strontium, molybdenum, tungsten, barium, niobium, zinc, nickel, manganese, a combination thereof or another compound. For example, the ceramic material containing lead magnesium-niobate, lead zirconate and lead titanate as the main components as well as lanthanum or strontium can be preferably used.

The piezoelectric film may be dense or porous. If it is porous, its porosity is preferably 40% or less.

Furthermore, the piezoelectric film 52 may have a single layer structure or a laminated structure of two or more layers. In the case of the laminated structure, the respective layers may be arranged horizontally or vertically.

In addition, the detecting portion may be disposed only on one side of the oscillating portion, or the detecting portions may be disposed on both the sides of the oscillating portion.

The first electrode 54 and the second electrode 56 inputs an electric signal from the piezoelectric film 52 to a pair of terminal pads by way of the pair of leads 58 and 60. The first electrode 54 is connected to the lead 58 by way of a connecting portion 55, which comes in contact with the piezoelectric film 52 but does not come in contact with the second electrode 56 and the lead 60. The second electrode 56, the leads 58, 60 and the terminal pads may be simultaneously formed by a thin film deposition technique such as printing.

The first and second electrodes are adjusted to an appropriate thickness in compliance with a use purpose, but their thickness is preferably in the range of 0.1 to 50 μm.

The first electrode is preferably made of an electrically conductive metal which is solid at room temperature. Examples of such a metal include aluminum, titanium, chromium, iron, cobalt, nickel, copper, zinc, niobium, molybdenum, ruthenium, rhodium, silver, tin, tantalum, tungsten, iridium, platinum, gold, lead and alloys thereof. Needless to say, an optional combination of these elements is also acceptable. Furthermore, there can suitably be used the electrode material containing, as the main component, a platinum group metal such as platinum, rhodium or palladium, or an alloy such as silver-platinum or platinum-palladium containing these platinum group metals. Moreover, copper, silver and gold are preferable, because of having a good durability.

The second electrode is preferably made of a high-melting metal such as platinum, ruthenium, rhodium, palladium, iridium, titanium, chromium, molybdenum, tantalum, tungsten, nickel, cobalt or an alloy thereof. Needless to say, an optional combination of these high-melting metals is also acceptable. Furthermore, there can suitably be used the electrode material containing, as the main component, a platinum group metal such as platinum, rhodium or palladium, or an alloy such as silver-platinum or platinum-palladium containing these platinum group metals. The second electrode is exposed to a high temperature sometimes during the heat treatment of the piezoelectric film, and therefore the second electrode is preferably made of the above-mentioned metal which can withstand a high-temperature oxidizing atmosphere.

Alternatively, the second electrode may be made of a thermite containing any of these high-melting metals and a ceramic material such as alumina, zirconium oxide, silicon oxide or glass.

No particular restriction is put on the profile of the ceramic substrate, and it is suitably selected in compliance with a use purpose. The profile of the ceramic substrate is preferably panel-like, but it may be rod-like or pipe-like.

According to the first aspect of the present invention, the resistance of a potentiometric resistor can be regulated by trimming, whereby the unevenness of the output voltage of a sensor can be reduced.

According to the second aspect of the present invention, the resistance of a serial resistor can be regulated by trimming, whereby the unevenness of the output voltage of a sensor can be reduced.

What is claimed is:

1. A sensor which comprises:

a ceramic substrate having a first end and a second end;

a sensing resistor, embedded in said ceramic substrate at said first end;

a first pair of leads connected to said sensing resistor to which an electric current can be applied through said first pair of leads;

a second pair of leads connected to said sensing resistor to detect a voltage across said sensing resistor by measuring the voltage between said second pair of leads; and a serial resistor disposed at said second end of said substrate, and electrically connected to said sensing resistor by means of one lead of said second pair of leads;

wherein a resistance of said serial resistor is trimmed so that a total resistance of said sensing resistor, said second pair of leads, and said serial resistor, has a proportional relation with a resistance of said sensing resistor of the output voltage circuit.

2. The sensor according to claim 1, wherein said total resistance is at least 100 times as great as the resistance of said sensing resistor.

3. The sensor according to claim 1, wherein said sensing resistor has a positive resistance temperature coefficient.

4. The sensor according to claim 1, wherein said sensing resistor is a semiconductor element having a resistance which changes in accordance with a gas concentration at the sensor.

5. The sensor according to claim 1, wherein said sensing resistor is a piezoelectric ceramic element for converting a mechanical stress into an electrical signal.

* * * * *